US005227519A

United States Patent [19]
Lin et al.

[11] Patent Number: 5,227,519
[45] Date of Patent: Jul. 13, 1993

[54] PRODUCTION OF CARBOXYLIC ACIDS FROM CARBONYLATION OF ALCOHOL

[75] Inventors: Ying-Chih Lin; Yeong-Cheong Lee, both of Taipei, Taiwan

[73] Assignee: China Petrochemical Development Corporation, Taipei, Taiwan

[21] Appl. No.: 840,175

[22] Filed: Feb. 24, 1992

[51] Int. Cl.$^5$ .............................................. C07C 51/12
[52] U.S. Cl. .................................................... 562/519
[58] Field of Search ................................ 562/519, 522

[56] References Cited

U.S. PATENT DOCUMENTS

| | | | |
|---|---|---|---|
| 3,769,329 | 10/1973 | Paulik et al. | 260/488 K |
| 4,628,041 | 12/1986 | Smith et al. | 562/519 |
| 4,690,912 | 9/1987 | Paulik et al. | 502/161 |
| 4,792,620 | 12/1988 | Paulik et al. | 562/519 X |
| 5,026,907 | 6/1991 | Wegman et al. | 562/519 |
| 5,155,261 | 10/1992 | Marston et al. | 562/519 X |

FOREIGN PATENT DOCUMENTS

| | | |
|---|---|---|
| 0055618 | 7/1982 | European Pat. Off. . |
| 74101387 | 5/1981 | Taiwan . |

OTHER PUBLICATIONS

J. Hjortkjaer et al., "Rhodium Complex Catalyzed Methanol Carbonylation. Effects of Medium and Various Additives", Ind. Eng. Chem., Prod. Res. Dev., vol. 16, No. 4, 1977, pp. 281-285.

B. L. Smith et al., "The Rhodium-Catalyzed Methanol Carbonylation to Acetic Acid at Low Water Concentrations: The Effect of Iodide . . . ", J. Molecular Catalysis, 39 (1987) pp. 115-136.

*Primary Examiner*—Arthur C. Prescott
*Attorney, Agent, or Firm*—Wegner, Cantor, Mueller & Player

[57] ABSTRACT

This invention relates to an improved process for synthesizing carboxylic acids by the carbonylation of alcohol. An alcohol such as methanol is reacted with carbon monoxide in a liquid reaction medium containing a rhodium (Rh) catalyst stabilized with an haloacetic acid, especially trifluoroacetic acid (TFAA), along with alkyl iodide such as methyl iodide (MeI) in specified proportions. The present reaction system is not only characterized by unexpectedly high catalyst stability, but also characterized by the high reaction rate for the formation of acetic acid. The improvement resides in the employment of trifluoroacetic acid as the catalyst promoter at a temperature from 180° C. to 200° C. The primary advantage of the catalyst system of this invention is the enhancement of the rate of carbonylation. The other advantage of the catalyst system is that they are readily soluble and thermally stable, making them resistant to deposition.

11 Claims, No Drawings

PRODUCTION OF CARBOXYLIC ACIDS FROM CARBONYLATION OF ALCOHOL

BACKGROUND OF THE INVENTION AND PERTINENT PRIOR ART

1. Field of the Invention:

This invention relates to an improvement of a process for synthesizing carboxylic acids by the carbonylation of alcohol. More particularity, this invention relates to the addition of trihaloacetic acid to the rhodium catalytic system to promote the reaction rate. The alcohol used in this reaction system has the formula of ROH, where R is a saturated hydrocarbonyl radical having 1 to 4 carbon atoms.

2. Description of the Prior Art:

The use of group VIII transition metals as the carbonylation catalysts for the production of carbonylation products are known in the art, with many of such catalysts being based on cobalt and using a halide promoter. However, the rhodium system has become the most important one in the recent years. So far as we know, there has not heretofore been a disclosure of a rhodium based carbonylation catalyst system containing trihaloacetic acid as the promoter used in the generation of carboxylic acid such as acetic acid by the carbonylation of alcohol such as methanol with carbon monoxide at mild pressure and temperature conditions. The rhodium catalytic systems that have been disclosed will be described in the following paragraphs and the relationship between those procedures and this invention will be discussed.

Among processes for synthesizing acetic acid, the one that is the most commercially useful is the carbonylation of methanol with carbon monoxide as taught in U.S. Pat. No. 3,769,329 and in U.S. Pat. No. 4,690,912 both issued to Paulik et al. on Oct. 30, 1973, and Sep. 1, 1987 respectively. The reaction was carried out at 180° C. and 35–70 Kg/cm$^2$ Co. The catalyst system comprises rhodium, either dissolved or otherwise dispersed in the liquid reaction medium or else supported on an inert solid, along with a halogen-containing catalyst promoter such as methyl iodide. The patents teach that the preferred solvent and liquid reaction medium for the process is the desired carboxylic acid itself, i.e., acetic acid when methanol is being carbonylated to produce acetic acid. The selectivity is exceptionally high, typically greater than 95%. However, the rate of carbonylation has been highly dependent on water concentration in the reaction medium. When the water concentration is reduced to below about 14–15 wt %, the rate of reaction declines. Reducing the water content also leads to the formation of by-product such as ester. It is taught in European Patent No. 0055618 that typically about 14–15% water is present in the reaction medium of a typical acetic acid-producing system using carbonylation technology. In a paper written by Hjortkjaer and Jensen [Ind. Eng. Chem., Prod. Res. Rev. 16,281 (1977)], it is shown that the reaction rate of methanol carbonylation is increased with the increasing of water content from 0 to 14 wt %. Above 14 wt %, the reaction rate is unchanged. The catalyst also becomes more susceptible to inactivation and precipitation when carbon monoxide partial pressure and/or water content is/are low. These prior arts disclose an important message that water must be present in the reaction system to obtain a satisfactory reaction rate.

Taiwan Application No. 74101387, to Celanese Corporation, disclose that using high concentration of LiI as the stabilizer for the rhodium catalytic system under a limited amount of water, it will be necessary to add methyl acetate as the promoter in order to obtain a productivity almost the same as the one which was obtained from a system with high concentration of water. The purpose of the Celanese patent is to reduce the amount of water but this also reduces the reaction rate.

It can be seen from the prior arts mentioned above that those systems either have the disadvantage of requiring high water content or have the disadvantage of the reduced reaction rate if the amount of water therein is reduced. Those literatures have never mentioned the use of trihaloacetic acid. Therefore, the main purpose of this invention is to find a suitable additive which can both reduce the amount of water and increase the reaction rate. Using the catalytic system of this invention, a very high productivity can be obtained under the reduce water content of 4 to 11% so that the problem resulting from water can be avoided. The catalytic system of this invention, even though dissolved in the system containing low amount of water, is still resistant to precipitation. Furthermore, in view of the separation of the acetic acid from low amount of water, the consumption of energy during distillation can be reduced when compared with the separation of them from high amount of water. The other procedures, such as solvent extraction, can also be simplified and thus the expansion of equipments can be avoided. The accomplishment of this invention, i.e., achieving high productivity and reaction rate under low water content by the incorporation of trifluoroacetic acid into the catalytic system, can not be overmatched by the prior art. According to the present invention, the reaction rate in the environment of low water content and in the absence of methyl acetate is even higher than that of the prior art in which methyl acetate is used.

DETAILED DESCRIPTION AND PREFERRED EMBODIMENTS

The catalyst system of this invention was employed in carbonylation reactions operated as a batch process. The reactor employed for the carbonylation reactions in this example consists of a corrosion-resistant main reaction vessel and a CO reservoir connected to the main reaction vessel with a regulator between them to keep a constant pressure in the main reaction vessel. The main reaction vessel was equipped with a magnetic drive stirrer and a methanol reservoir on the top of a sample inlet. Heat was provided by heating mantle wrapping on the reactor walls. An inlet valve for liquid reactants was provided on the top of the reactor and the gaseous reactants enter the reactor through the same inlet. The effluent from the reaction was withdrawn through a dip tube.

The temperature at which the reaction is effected is in the range from 50° C. to 300° C. with higher temperature favoring higher reaction rates. The preferred temperature range is from 125° C. to 225° C. The reactor temperature was between about 190° C. and 195° C. Reaction pressure may vary over a wide range. Partial pressure of carbon monoxide from 1 to 70 kg/cm$^2$ or even higher can be employed. However, the process is particularly advantageous in that it can be carried our at a lower carbon monoxide partial pressure ranging from 1 to 21 kg/cm$^2$ or even more preferably at carbon monoxide partial pressure ranging from 3 to 71 kg/cm$^2$. The liquid reaction medium used in the reaction system was acetic acid.

In this operation, the reactants are charged into the reactor that contains the liquid catalyst system which is then subjected to the desired temperature and pressure conditions. To make quantitative comparison on the reaction rate, the rate data is reported as space time yield as suggested by Smith, B. L. et al. in J. Mol. Cataly. 39, 115, 1987. The space time yield (STY) is expressed in gram-moles of acetic acid produced per hour per liter of reaction medium contained in the carbonylation reactor, the volume of reaction medium being measured at ambient temperature and in the unaerated state. The present invention is illustrated in the following examples which, however, are not to be construed as limiting the invention since various changes and modifications within the spirit of the invention will become apparent to those skilled in the art.

COMPARATIVE EXAMPLES 1 and 2

In order to compare this invention with those prior arts to show the superiority of this invention, the prior arts are repeated. The results are shown in Table I as the Comparative Examples. In these two examples, no trifluoroacetic acid was used. In Comparative Example 2, 14% LiI was added. The experimental procedures for both Comparative Examples are similar to those for Example 1 and will be described below.

TABLE I

| REAGENTS | Comparative Example 1 High water No TFAA No LiI | Comparative Example 2 Low water No TFAA With LiI |
|---|---|---|
| water % | 14 | 8 |
| TFAA % | 0 | 0 |
| LiI % | 0 | 14 |
| MeI % | 14 | 14 |
| Rh | 400 ppm | 400 ppm |
| STY | 10.79 | 12.77 |

EXAMPLES

In the following examples, the main reactors used in the experiment is Hatelloy B. The % represents weight percentage.

EXAMPLE 1

The reactor was charged with a solution containing rhodium iodide, methyl iodide, water, acetic acid and trifluoroacetic acid (TFAA) in proportions to provide 400 ppm rhodium, 14.0% methyl iodide, 14.0% water and 20.0% TFAA. The reactor was sealed, pressured to approximately 28.14 Kg/cm² of carbon monoxide partial pressure which was checked at 25° C. The reactor was then slowly vented of its carbon monoxide and then flushed twice with carbon monoxide (7 Kg/cm²). The reactor was then pressureed to 14 Kg/cm² with carbon monoxide and heated to 120° C. for 2 hours, after which the agitator was turned on to stir at medium speed (100–200 rpm). The reactor was then further heated to 194° C., stirred at high speed (500–600 rpm) and pressured with carbon monoxide to 29 Kg/cm². The reactor was maintained at a temperature of 194° C. when methanol was fed into the solution and carbon monoxide was introduced continuously at a rate to maintain the pressure in the reactor at about 29 Kg/cm². The rate of reaction was determined by monitoring the amount of carbon monoxide consumed over a period of time, assuming that the ideal gas law can be applied to carbon monoxide. The rate of CO consumption approximates to the rate of acetic acid production since the formation of by-products is small as shown by products analysis.

The analysis of the carbonylation product recovered showed that all the methanol was converted to acetic acid. Selectivity for the formation of carboxylic acid product is greater than 95%. No substantial amounts of by-products such as aldehydes, dimethyl ether, high boiling point carboxylic acid, methane and carbon dioxide are detected by gas chromatography. It took about 10 minutes to convert 50% of methanol to acetic acid. The results are listed in Table II. Compared with Comparative Example 1, it is clear the STY value of Example 1, wherein 20% trifluoroacetic acid is added, has been increased about 50%.

TABLE II

| REAGENTS | High water High TFAA No LiI |
|---|---|
| water % | 14 |
| TFAA % | 20 |
| LiI % | 0 |
| MeI % | 14 |
| Rh | 400 ppm |
| STY | 15.08 |

EXAMPLE 2

Acetic acid was prepared by the method of Example except that the water concentration was reduced to 8% and 14% LiI was added. The rate of reaction was again determined by monitoring the amount of carbon monoxide consumed over a period of time. No substantial amounts of by-products are detected by gas chromatography. The results are listed in Table III. It is clear that the STY value of this example is higher than those of Comparative Examples and is also higher than that of Example 1. It can be learned from this example that if both LiI and trifluoroacetic acid are added to the reaction system, not only water content can be reduced, but also reaction rate is increased.

TABLE III

| REAGENTS | Low water High TFAA with LiI |
|---|---|
| water % | 8 |
| TFAA % | 20 |
| LiI % | 14 |
| MeI % | 14 |
| Rh | 400 ppm |
| STY | 19.79 |

EXAMPLES 3–6

Acetic acid was prepared by the method of Example 1 except the molar ratio of trifluoroacetic acid to acetic acid was varied. The rate of reaction was again determined by monitoring the amount of carbon monoxide consumed over a period of time. No substantial amounts of by-products are detected by gas chromatography. The results are listed in Table IV. As can be clearly seen in the Table IV, the rate of formation of acetic acid is increased with the increasing of the wt % of trifluoroacetic acid. The STY value was almost doubled when the wt % of TFAA is increased from 10% to 25%. The solution remained clear after exposed to air for about 2 weeks, no precipitation was observed. The amount of soluble rhodium metal was determined by atomic absorption as described in EXAMPLES 13-17 below.

TABLE IV

|  | Comparative Example 2 | Example 3 | Example 4 | Example 5 | Example 6 |
| --- | --- | --- | --- | --- | --- |
| water % | 8 | 8 | 8 | 8 | 8 |
| TFAA % | 0 | 10 | 15 | 20 | 25 |
| LiI % | 14 | 14 | 14 | 14 | 14 |
| MeI % | 14 | 14 | 14 | 14 | 14 |
| Rh | 400 ppm | 400 ppm | 400 ppm | 400 ppm | 400 ppm |
| STY | 12.77 | 13.83 | 18.16 | 19.79 | 23.17 |

EXAMPLES 7-12

The purpose of these examples is to test the activity of the catalytic system after consecutive use. A batch reactor was charged with appropriate amounts of rhodium iodide, methyl iodide, LiI and trifluoroacetic acid. The solvent is acetic acid. The reaction was operated under the conditions as described in Example 1. The rate of reaction was again determined by monitoring the amount of carbon monoxide consumed over a period of time. The STY values are listed in Table V as STY1. After methanol was all consumed and CO pressure of the reservoir remained constant, a second aliquot of methanol was added to test the activity of the catalyst system. Since the concentration of rhodium catalyst decreased when the formation of acetic acid increased, a lower STY value was expected and listed in Table V as STY2. The STY2* values are the STY value after correction for the concentration of Rh (STY2*=-STY1× correction factor). Gas chromatographic analysis showed that the resultant reaction mixture contains acetic acid and methyl iodide. It is obvious from the table, the activity of the catalyst system after the first aliquot of methanol was completely converted was almost the same as its initial activity, which can be verified by the small difference between STY2 and STY2*.

TABLE V

|  | Example 7 | Example 8 | Example 9 | Example 10 | Example 11 | Example 12 |
| --- | --- | --- | --- | --- | --- | --- |
| water % | 8 | 8 | 8 | 8 | 8 | 8 |
| TFAA % | 0 | 20 | 0 | 15 | 25 | 30 |
| LiI % | 0 | 0 | 14 | 14 | 14 | 14 |
| MeI % | 14 | 14 | 14 | 14 | 14 | 14 |
| Rh | 400 ppm | 400 ppm | 400 ppm | 400 ppm | 400 ppm | 400 PPm |
| STY1 | 9.67 | 10.42 | 12.61 | 18.16 | 24.26 | 21.93 |
| STY2 | 6.65 | 6.92 | 8.96 | 11.17 | 13.80 | 11.70 |
| STY2* | 8.23 | 7.39 | 8.68 | 10.08 | 13.13 | 11.78 |

*The theoretical STY value after correction of rhodium concentration reduction and volume increase.

EXAMPLES 13-17

The purpose of this experiment is to test solubility of the rhodium catalytic system. The reuslts showed that a reaction system consisting of suitable concentration of trifluoroacetic acid and LiI still has the same solubility after settled for a period of time. The experimental procedure are as follows: A mixture of 8% $H_2O$, 14% MeI, 25% trifluoroacetic acid and Rh, in which the concentration of Rh was always kept at 400 ppm, was charged into the reactor and the reactor was sealed and heated to 194° C. for one hour and then allowed to be kept at room temperature. The solution in the reactor was then removed and then sealed in a flask for 5 to 10 days. The concentration of Rh in the clean solution was then determined by using the atomic absorption spectrum. The results listed in Table VI showed that the concentration of Rh was in the range from 394 to 342 ppm. It is seen from this table that the extent of precipitation is very low.

TABLE VI

| Example | Original Rh Concentration | New Rh Concentration |
| --- | --- | --- |
| 13 | 400 ppm | 394 ppm |
| 14 | 400 ppm | 371 ppm |
| 15 | 400 ppm | 342 ppm |
| 16 | 400 ppm | 380 ppm |
| 17 | 400 ppm | 358 ppm |

In a word, with the addition of trifluoroacetic acid and LiI, this invention not only increases the rate to almost twice as fast as that of the prior art, but also allows the reduction of the water content. Another advantages of this invention are that the catalytic system has high solubility and is very stable even at high temperature, making it resistant to precipitation.

What is claimed is:

1. A carbonylation process for production of carboxylic acid, which comprises contacting an alcohol of formula ROH wherein R is a saturated hydrocarbonyl radical having from 1 to 4 carbon atoms, with carbon monoxide in the presence of a catalyst system consisting essentially of (1) a rhodium compound, (2) a halogen providing component, (3) an iodide salt, and (4) a separately added trihaloacetic acid promoter component.

2. The process of claim 1, wherein said halogen providing component is an iodine providing component.

3. The process of claim 2, wherein said iodine providing component is methyl iodide.

4. The process of claim 1, wherein said trihaloacetic acid component is trifluoroacetic acid.

5. The process of claim 1, wherein said iodide salt is lithium iodide.

6. The process or claim 1, wherein said alcohol is methanol.

7. The process of claim 1, wherein said process is carried out at a temperature form about 180° C. to 220° C.

8. The process of claim 1, wherein the partial pressure of carbon monoxide is in the range from about 1.4 to about 60 kg/cm².

9. The process of claim 4, wherein the concentration of trifluoroacetic acid is from 2 to 40 weight percentage.

10. The process of claim 5, wherein the concentration of lithium iodide is from 2 to 40 weight percentage.

11. The process of claim 1, wherein said process is carried out at a water concentration from 4 to 11 weight percentage.

* * * * *